United States Patent [19]  [11] 3,954,828
Fridinger  [45] May 4, 1976

[54] PERFLUOROALKANESULFONATE ESTER HERBICIDES

[75] Inventor: Tomas L. Fridinger, Woodbury, Minn.

[73] Assignee: Tomas L. Fridinger, St. Paul, Minn.

[22] Filed: May 8, 1975

[21] Appl. No.: 575,648

Related U.S. Application Data

[60] Division of Ser. No. 336,956, March 1, 1973, Pat. No. 3,907,853, which is a continuation-in-part of Ser. No. 27,998, April 13, 1970, abandoned.

[52] U.S. Cl............................................. 260/456 P
[51] Int. Cl.² ........................................ C07C 143/68
[58] Field of Search ...................... 260/456 F, 456 P

[56] References Cited

UNITED STATES PATENTS 3,346,612  10/1967  Hansen ............................ 260/456 F
3,832,409  8/1974  Endres et al. ................... 260/456 F

*Primary Examiner*—James O. Thomas, Jr.
*Assistant Examiner*—Nicky Chan
*Attorney, Agent, or Firm*—Alexander, Sell, Steldt & DeLaHunt

[57] ABSTRACT

Perfluoroalkanesulfonate esters of methyl- thio-, methylsulfinyl- or methylsulfonyl-substituted phenols. The compounds are herbicides.

6 Claims, No Drawings

PERFLUOROALKANESULFONATE ESTER HERBICIDES

This application is a division of my application Ser. No. 336,956, filed Mar. 1, 1973, now U.S. Pat. No. 3,907,853; which is a continuation-in-part of my application Ser. No. 27,998, filed Apr. 13, 1970, now abandoned.

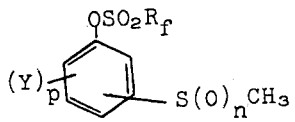

The present invention relates to compounds which are aryl esters of trifluoromethanesulfonic acid and perfluoroethanesulfonic acids.

Briefly, the invention relates to perfluoroalkanesulfonate compounds of the formula

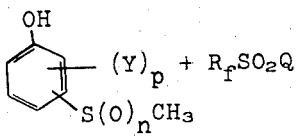

Formula I wherein $R_f$ is a trifluoromethyl or perfluoroethyl group, $n$ is zero, one or two, each Y independently is an alkyl group having one or two carbon atoms or chlorine and $p$ is an integer of from 0 to 3 inclusive, $p$ being zero or one when $n = 2$. It is understood that Y may be in positions 2, 3, 4, 5 or 6 and preferably at 3, and the $-S(O)_nCH_3$ is at either 2, 3, 4, 5 or 6, but preferably at 4.

Compounds of Formula I above wherein $R_f$ is trifluoromethyl or perfluoroethyl are active herbicides, but generally no substantial increase in herbicidal activity is observed for compounds wherein $R_f$ contains two carbon atoms rather than one. For reasons of economy, compounds of the present invention wherein $R_f$ is trifluoromethyl are preferred. Especially preferred are those compounds wherein $p$ is zero or one. Of great importance is the fact that each compound of the invention contains, as substituents, a methyl group bonded through a sulfur atom to the phenyl nucleus, and a perfluoroalkanesulfonoxy group. All of the compounds exhibit herbicidal activity. Some have activity against insects and other pests.

Compounds of the invention wherein $n$ is zero are prepared by reacting appropriately substituted phenols with a perfluoroalkanesulfonylating agent such as trifluoromethanesulfonyl fluoride. Compounds of the invention wherein $n$ is one or two are prepared by selective oxidation of compounds of Formula I wherein $n$ is zero.

The phenols used as intermediates for the preparation of the compounds of the invention wherein $n$ is zero are known in the art, or can easily be prepared by known methods. Methylthio-substituted phenols, for example, may be prepared by reacting dimethylsulfoxide with phenols followed by thermal degradation, as described in Bull. Soc. Chim. Belg., 73, 546 (1964); or by the well-known method involving methylation of mercapto-substituted phenols using methyl iodide, dimethyl sulfate, and the like. Yet another method involves the reaction of phenols with dimethyl disulfide and sulfuryl chloride as described in German Pat. No. 1,063,177.

The general method for the preparation of compounds of the invention is represented by Equation 1 below, and is preferred for the preparation of compounds of the invention wherein $n$ is zero.

EQUATION 1

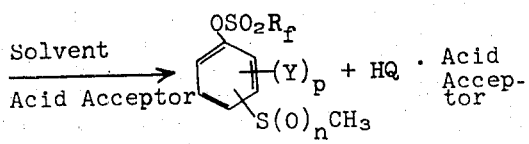

$R_f$, Y, $p$ and $n$ are as defined hereinabove and $R_fSO_2Q$ is $CF_3SO_2F$, $CF_3SO_2Cl$, $(CF_3SO_2)_2O$, $CF_3CF_2SO_2Cl$ or $CF_3CF_2SO_2F$. A solvent is not required, but may be convenient for small volume reactions. The solvents useful for this reaction must be substantially non-reactive under the reaction conditions used and include 1,2-dimethoxyethane, benzene, chloroform, dichloromethane, tetrahydrofuran, dimethylformamide, dimethylacetamide, dimethylsulfoxide, acetone and the like. This method is similar to the method disclosed in U.S. Pat. No. 3,346,612.

Although use of an acid acceptor is not essential, it will generally simplify isolation of the desired product in good purity, and for this reason acid acceptors are ordinarily used. Preferred acid acceptors include tertiary amines such as pyridine, triethylamine, N,N-dimethylaniline, tetramethylethylenediamine and the like. Inorganic bases such as sodium carbonate, sodium acetate, sodium hydroxide and the like may also be employed as acid acceptors. When perfluoroalkanesulfonyl fluoride is employed as a reactant, the acid acceptor should have a $pK_b$ value of about 6 or lower.

The reaction of Equation 1 generally proceeds satisfactorily at room temperature. Cooling may be necessary to maintain control of rapid reactions, and occasionally refluxing and/or extended reaction times may be necessary to promote reaction. Thus reaction temperatures are not critical, and the techniques commonly used in the art suffice to control reaction conditions.

Because the perfluoroalkanesulfonylating reaction is often run under rather strongly basic conditions, it may be desirable to provide a nonoxidizing atmosphere above the reaction mixture when moderately readily oxidized phenols are used. Such an atmosphere may conveniently be provided by flushing the system continuously with nitrogen, or by other equivalent procedures apparent to those skilled in the art. Base, if any, may be removed after reaction by such methods as distillation, washing with water, washing with dilute aqueous acid, etc. The compounds of the invention wherein $n$ is zero are generally high boiling liquids and may be isolated and purified by conventional methods such as distillation, extraction and vapor phase or elution chromatography.

The compounds of the invention are aromatic compounds which exhibit excellent stability, and accordingly they may be used as heat-transfer media and the like. Although they may be decomposed or reacted under vigorous conditions, in many cases they can be substituted to form derivatives by classical aromatic reactions of organic chemistry, e.g., by halogenation, to introduce substituent groups on the aromatic ring.

Compounds of the invention wherein $n$ is one or two are prepared by selective oxidation of the methylthio-substituted compounds of the invention. In such compounds the perfluoroalkanesulfonoxy group is quite stable to oxidation conditions generally known to be useful for oxidation of alkylthio groups to alkylsulfinyl and alkylsulfonyl groups, and the methods used and known in the art for said oxidations are thus generally applicable. Oxidizing agents such as peracids, (e.g., peracetic acid, meta-chloroperbenzoic acid, perbenzoic acid and the like), sodium metaperiodate and hydrogen peroxide have been found useful. Peracetic acid has been used routinely with success and is preferred. The compounds of the invention wherein $n$ is one or two may be liquids or solids, and may be purified by conventional methods.

Standard screening methods in preemergence tests with grasses and broadleaves have surprisingly shown the compounds of the invention to be active herbicides, for example, against one or more representative grasses or broad-leaved weeds of the following:

| Abbreviation | Botanical Name | Common Name |
| --- | --- | --- |
| FT | Setaria Taberi | Giant Foxtail |
| CR | Digitaria Ischaemum | Crab Grass |
| QC | Agropyron Repens | Quack Grass |
| CG | Bromus Sicalinus | Cheat Grass |
| OG | Dactylis Glomerata | Orchard Grass |
| WM | Brassica Kaber | Wild Mustard |
| VL | Arbutilon Theophrasti | Velvet Leaf |
| BW | Convolvulus Arvensis | Field Bird Weed or Wild Morning Glory |
| PW | Amaranthus Retroflexus | Pigweed |

The preferred compounds are those which show good herbicidal activity at 5 pounds/acre or less, and include the compounds of Table I.

TABLE I 3-methyl-4-methylthiophenyl trifluoromethanesulfonate
4-methylthiophenyl trifluoromethanesulfonate
4-methylsulfonylphenyl trifluoromethanesulfonate
4-methylthiophenyl perfluoroethanesulfonate
3-methyl-4-methylthiophenyl perfluoroethanesulfonate
4-methylsulfonylphenyl perfluoroethanesulfonate
2,3-dimethyl-4-methylthiophenyl trifluoromethanesulfonate
2-methyl-4-methylthiophenyl trifluoromethanesulfonate
2-methyl-4-methylsulfonylphenyl trifluoromethanesulfonate
3-methyl-4-methylsulfinylphenyl trifluoromethanesulfonate
4-methylsulfinylphenyl trifluoromethanesulfonate
3-ethyl-4-methylthiophenyl trifluoromethanesulfonate In order to control unwanted plants, the compounds of the invention can, if desired, be used alone as herbicides (for example as dusts or granules of the compounds if they are solids). Preferably, however, herbicidal formulations which contain the compounds of the invention in a horticulturally acceptable extending medium are employed. These formulations may include one or more active ingredients plus herbicidal adjuvants, carriers, and the like.

The compounds of the invention may be formulated as wettable powders, emulsifiable concentrates, aqueous or non-aqueous solutions and suspensions, granules, dusts and the like. The compounds can be finely divided and dispersed or suspended in any of the usual aqueous media. Spreading agents, wetting agents, sticking agents, or other adjuvants can be added as desired. Specific formulations may be desired to achieve specific biological objectives such as controlling herbicide availability, improving adhesion to plants, etc., and herbicidal formulation techniques for accomplishing such objectives are generally known to the art.

The compounds of the present invention preferably are employed in the form of emulsifiable concentrates and can be present (in such concentrates) in concentrations of about 5% to 60% weight percent or more, depending upon solubility. The compounds of the invention are soluble in such common organic horticultural solvents as benzene, toluene, xylene, dichloromethane, chloroform, hexane and heptane. Less highly refined aromatic or aliphatic hydrocarbons and mixtures thereof may be employed as solvents, such as coal tar fractions, straight run petroleum distillates, thermolytically or catalytically cracked hydrocarbon oil, gas oil, light lubricating oil fractions, kerosene, mineral seal oil, and the like. In appropriate cases, oxygenated solvents such as ketones may be employed.

Emulsifiable concentrates can be dispersed in water to permit their use in an aqueous spray. A small amount of an organic surface active agent capable of lowering the surface tension of water is preferably employed to increase emulsion stability.

Examples of surface agents (commonly known as dispersing agents, wetting agents or emulsifying agents) comprise soft or hard soaps; morpholine or dimethylamine oleate; sulfonated castor, petroleum and fish oils; sodium salts of lignin sulfonic acid; alkylated aromatic sodium sulfonates, such as decylbenzene sodium sulfonate, dodecylbenzene sodium sulfonate; butyl or other amine salts of decyl or dodecyl benzene sulfonic acid; sodium lauryl sulfate; disodium monolauryl phosphate; ethylene oxide condensation products of alkyl phenols such as octyl phenol; ethylene oxide condensation products of tall oil, and ethylene oxide condensation products of higher alcohols or higher mercaptans. Mixtures of two or more surface active agents may be employed. Generally, surface active agents will comprise only a small proportion of the composition.

The formulation of dry compositions for application as granules, dusts or for further dilution with liquid carriers is readily accomplished by mixing the compounds of the invention with solid carriers. Such solid carriers may be of various sizes from dust to granules. Suitable carriers include charcoal, talc, clay, pyrophyllite, silicas, fuller's earth, lime, diatomaceous earth, flours such as walnut shell, wheat, soya bean, cottonseed and wood flours, magnesium and calcium carbonate, calcium phosphate and the like. The techniques for producing such formulations are well known to the art. Powders may be granulated by the use of suitable binders such as cellulose derivatives, for example ethyl cellulose or carboxymethyl cellulose, corn syrup, and the like. Dry formulations may be applied by spraying, spreading, dusting or the like.

Although herbicidally effective amounts of compounds of the present invention vary widely, the more herbicidally active compounds of the invention exhibit satisfactory control of broadleaf and grass weeds at an application rate of 5 pounds per acre or less.

It is of course to be expected that local conditions of temperature, humidity, moisture content of the soil, nature of the soil, and the like, will affect the required application rate. Effective resolution of these factors is within the skill of those versed in the herbicidal art.

The herbicidal compositions of the invention may contain one or more of the herbicidal compounds set out hereinbefore as the sole active species, or they may contain in addition thereto various other biologically active substances. Insecticides and fungicides, for example, may be incorporated in the compositions. Further, if desired, the herbicidal compositions may include fertilizers, trace metals or the like and when applied directly to the soil may additionally include such ingredients as nematicides, soil conditioners, plant growth regulators and herbicides of similar or different properties.

Many of the compounds of the invention have been found to be active as insecticides using standard screening methods. Activity has been shown against the following insects: mosquito larvae, houseflies, bollworm (systemic), boll weevil (foliar and systemic) and German cockroach.

The invention may be more fully appreciated by reference to the following illustrative examples.

EXAMPLE 1

Thirty grams (0.20 moles) of trifluoromethanesulfonyl fluoride are bubbled over a 20 minute period into a stirred solution of 3-methyl-4-methylthiophenol (15.4 g., 0.10 mole) and triethylamine (11 g., 0.11 mole) in acetone (200 ml.) in a flask fitted with a dry ice condenser. The mixture is maintained under a nitrogen atmosphere while stirring at room temperature for 1 hour, and is allowed to stand overnight. The solution is then poured into water (250 ml.) and the resulting mixture is extracted with two 125 ml. portions of dichloromethane. The combined dichloromethane extracts are washed with two 125 ml. portions of water and dried over magnesium sulfate. The solvent is evaporated in vacuo and the orange liquid residue is fractionally distilled under aspirator vacuum. The fraction boiling at 143°–144°C., 3-methyl-4-methylthiophenyl trifluoromethanesulfonate, is collected.

Analysis: Calculated for $C_9H_9F_3O_3S_2$: C, 37.7; H, 3.2; Found: C, 38.0; H, 3.3.

It is effective against several weeds at a rate of 5 lbs/acre, notably, using abbreviations from above and percent effectiveness, 90/FT, 95/CR, 95/QC, 80/CG, 60/WM, 60/PW.

EXAMPLE 2

Twenty grams (0.13 mole) of gaseous trifluoromethanesulfonyl fluoride is added over a 15 minute period to a stirred solution under nitrogen atmosphere of 4-methylthiophenol (14.0 g., 0.10 mole), triethylamine (11 g., 0.11 mole) and acetone (200 ml.) in a flask fitted with a dry ice condenser. The mixture is stirred for 1 hour and is allowed to stand overnight. The solution is then poured into 250 ml. of water and the resulting mixture is then extracted with two 125 ml. portions of dichloromethane. The combined dichloromethane extracts are washed with two 125 ml. portions of water and dried over magnesium sulfate. The solvent is evaporated in vacuo and the orange liquid residue is distilled under aspirator vacuum. The fraction boiling at 134°–136°C., 4-methylthiophenyl trifluoromethanesulfonate, is collected.

Analysis: Calculated for $C_8H_7F_3O_3S_2$: C, 35.3; H, 2.6; Found: C, 35.3; H, 2.7.

The material shows herbicidal activity at 5 lbs/acre using the representational method of Example 1, 100/FT, 95/CR, 100/QC, 100/CG, 100/WM, 100/PW.

EXAMPLES 3–12

Other exemplary compounds of the invention prepared according to the method of Examples 1 and 2 (by treating the correspondingly substituted methylthiophenol with either trifluoromethylsulfonyl fluoride or perfluoroethylsulfonyl fluoride) are listed in Table II. Herbicidal activities of many are indicated, using the method above at 5 lbs/acre except for Examples 4 and 5 at 10 lbs/acre.

TABLE II

| Example No. | Compound | Boiling Point (°C/mm. Hg.) |
|---|---|---|
| 3 | 3-methyl-4-methylthiophenyl perfluoroethanesulfonate 70/FT, 90/CR, 90/QC, 90/CG, 50/WM | 95–97/0.1 |
| 4 | 4-methylthiophenyl perfluoroethanesulfonate 50/FT, 50/CR, 50/QC, 90/CG, 60/WM | 83–87/0.15 |
| 5 | 2,3-dimethyl-4-methylthiophenyl trifluoromethanesulfonate 80/FT, 100/CR, 100/QC, 90/CG, 50/WM | 80–83/0.1 |
| 6 | 2-methyl-4-methylthiophenyl trifluoromethanesulfonate 90/FT, 90/CG | 71–74/0.1 |
| 7 | 2,5-dimethyl-4-methylthiophenyl trifluoromethanesulfonate | 79–80/0.1 |
| 8 | 2-methylthiophenyl trifluoromethanesulfonate | 140–141/20 |
| 9 | 2-chloro-5-methyl-4-methylthiophenyl trifluoromethanesulfonate | 87/0.1 |
| 10 | 2,6-dimethyl-4-methylthiophenyl trifluoromethanesulfonate | 81–83/0.1 |
| 11 | 3-ethyl-4-methylthiophenyl trifluoromethanesulfonate 100/Ft, 95/CR, 100/QC, 100/OG, 100/WM, 90/BW | 87–90/0.35 |
| 12 | 4-methylthio-2,3,6-trimethylphenyl trifluoromethanesulfonate | 87–89/0.1 |

EXAMPLE 13

Hydrogen peroxide (13.6 g., 0.12 mole, 30%) is added dropwise over a fifteen minute period to a stirred, ice-bath-cooled solution of 4-methylthiophenyl trifluoromethanesulfonate (8.3 g., 0.03 mole) in 75 ml. of acetic acid. The mixture is stirred cold for 15 minutes and is then heated to reflux and maintained at the reflux temperature for 3 hours. Water (50 ml.) is added and the hot solution is filtered. The cold filtrate is diluted with water until turbid (25 ml.) and cooled overnight. White crystals of 4-methylsulfonylphenyl trifluoromethanesulfonate are collected by filtration, washed with water and dried, m.p. 86.5°–88.5°C.

Analysis: Calculated for $C_8H_7F_3O_5S_2$: C, 31.6; H, 2.3; Found: C, 31.7; H, 2.3.

This material is active as a herbicide at 5 lbs/acre as follows: 100/FT, 100/CR, 100/QC, 100/CG, 100/WM, 90/VL.

The same procedure is applied to other compounds of Examples 1–11.

EXAMPLE 14

To an ice-bath-cooled solution of 3-methyl-4-methylthiophenyl trifluoromethanesulfonate (5.67 g., 0.020 mole) in 57 ml. of glacial acetic acid is added dropwise with stirring 2.27 g. (0.020 mole) of hydrogen peroxide (30%). After stirring cold for 1 hour the mixture is stirred overnight at room temperature. The solution is poured into 200 ml. of water. The aqueous solution is then extracted with three 100 ml. portions of dichloromethane. The combined dichloromethane extracts are dried over magnesium sulfate, filtered, and the dichloromethane evaporated in vacuo. The residue is fractionally distilled to give 3-methyl-4-methylsulfinylphenyl trifluoromethanesulfonate, b. pt. 117°–121° C./0.2 mm. Hg.

Analysis: Calculated for $C_9H_9F_3O_4S_2$: C, 35.8; H, 3.0; Found: C, 36.0; H, 3.0.

The activity as a herbicide at 5 lbs/acre is: 100/FT, 80/CR, 100/QC, 80/CG, 100/WM, 30/BW.

The same procedure is applied to other compounds of Examples 1–11.

EXAMPLES 15–23

Other compounds of the invention prepared according to the method of Examples 3 and 4 are listed in Table III. In each Example, the correspondingly substituted methylthiophenyl perfluoroalkanesulfonate is the starting material. Activities as herbicides at 5 lbs/acre are represented as in Table II for certain of these materials.

TABLE III

| Example No. | Compound | Boiling Point (in °C/mm. Hg) or Melting Point (°C) |
| --- | --- | --- |
| 15 | 4-methylsulfonylphenyl perfluoroethanesulfonate 90/FT, 100/CR, 100/QC, 100/CG, 50/WM | 71–73 |
| 16 | 3-methyl-4-methylsulfonylphenyl perfluoroethanesulfonate | 77–79 |
| 17 | 4-methylsulfinylphenyl trifluoromethanesulfonate 90/FT, 50/CR, 50/QC, 90/OG, 90/WM, 100/BW | 115–117/0.3 |
| 18 | 3-methyl-4-methylsulfonylphenyl trifluoromethanesulfonate | 47–49 |
| 19 | 2-methylsulfonylphenyl trifluoromethanesulfonate | 81–83 |
| 20 | 2,3-dimethyl-4-methylsulfonylphenyl trifluoromethanesulfonate | 64–66 |
| 21 | 2-methyl-4-methylsulfonylphenyl trifluoromethanesulfonate 100/Ft, 100/Cr, 100/QC, 90/OG, 80/WM, 90/BW. | 78–80 |
| 22 | 2-chloro-5-methyl-4-methylsulfonylphenyl trifluoromethanesulfonate | 85–86 |
| 23 | 2,6-dimethyl-4-methylsulfonylphenyl trifluoromethanesulfonate | 114–116 |

Other compounds of the invention are readily prepared using the procedures described above in Examples 1–23 with the appropriate starting materials as will be evident after reading this disclosure. Most of the above materials which have no indicated herbicidal activity display activity at 40 lbs/acre, expressed as the average for four grasses (FT, CR, QC and OG) expressed as Example/average activity as: 7/50, 8/90, 9/80, 10/60, 12/60, 16/30, 18/90, 19/80, 20/80, 22/80, 23/40.

EXAMPLE 24

An emulsifiable concentration may be formulated from the following ingredients:

| Component | Lbs. |
| --- | --- |
| 4-methylsulfonylphenyl trifluoromethanesulfonate | 1.00 |
| surfactant (3/2 wgt. ratio of calcium salt of dodecylbenzenesulfonic acid and octylphenol ethylene oxide condensate having average of nine ethylene oxide units/molecule) | 0.5 |
| Xylene | 6.16 |

This concentrate has excellent emulsification characteristics and has a specific gravity of about 0.92 at 25°C. When emulsified at a rate of 1 gallon of emulsifiable concentrate per 10 gallons of water and sprayed on a plot of peanuts prior to emergence thereof at a rate of 2.5 pounds of 4-methylsulfonylphenyl trifluoromethanesulfonate per acre, it is found to be effective as a herbicide for the control of unwanted grasses and broadleaves.

What is claimed is:

1. A compound of the formula:

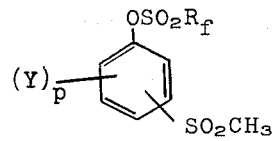

wherein $R_f$ is $CF_3$ or $C_2F_5$, each Y independently is chlorine or an alkyl group having 1 or 2 carbon atoms and $p$ is zero, 1 or 2.
2. The compound of claim 1 of the formula:
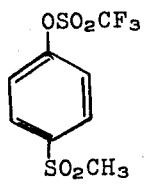
3. The compound of claim 1 of the formula:
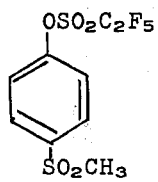
4. The compound of claim 1 of the formula:
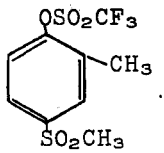
5. The compound of claim 1 of the formula:
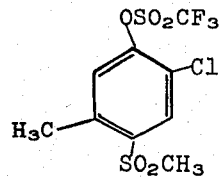
6. The compound of claim 1 of the formula:
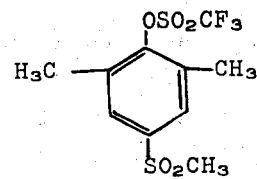
* * * * *

UNITED STATES PATENT AND TRADEMARK OFFICE
CERTIFICATE OF CORRECTION

PATENT NO. : 3,954,828
DATED : May 4, 1976
INVENTOR(S) : Tomas L. Fridinger

It is certified that error appears in the above-identified patent and that said Letters Patent are hereby corrected as shown below:

Cover page, under [73] the assignee of record, "Tomas L. Fridinger, St. Paul, Minn." should read -- Minnesota Mining and Manufacturing Company, St. Paul, Minn. -- .

Column 4, line 31, -- active -- should be inserted between "surface" and "agents".

Signed and Sealed this

Twenty-sixth Day of October 1976

[SEAL]

Attest:

RUTH C. MASON
Attesting Officer

C. MARSHALL DANN
Commissioner of Patents and Trademarks